United States Patent [19]

Morris, Sr. et al.

[11] Patent Number: 5,411,023

[45] Date of Patent: May 2, 1995

[54] OPTICAL SENSOR SYSTEM

[75] Inventors: G. Ronald Morris, Sr.; G. Ronald Morris, Jr., both of Bay Shore, N.Y.; Charles E. McMillen, Versailles, Ky.

[73] Assignee: The Shielding Corporation, Wilmington, Del.

[21] Appl. No.: 158,621

[22] Filed: Nov. 24, 1993

[51] Int. Cl.$^6$ .............................. A61B 5/00
[52] U.S. Cl. ................ 128/633; 128/653.5; 128/666; 356/41
[58] Field of Search .............. 128/633–634, 128/664–666, 653.1; 356/41

[56] References Cited

U.S. PATENT DOCUMENTS

| Re. 33,643 | 7/1991 | Isaacson et al. | |
|---|---|---|---|
| 4,167,331 | 9/1979 | Nielsen . | |
| 4,407,290 | 10/1983 | Wilber . | |
| 4,901,141 | 2/1990 | Costello . | |
| 4,951,674 | 8/1990 | Zanakis et al. | |
| 4,972,836 | 11/1990 | Schenck et al. | |
| 5,159,929 | 11/1992 | Morris et al. | 128/633 |
| 5,190,038 | 3/1993 | Polson et al. | |
| 5,246,002 | 9/1993 | Prosser . | |
| 5,273,041 | 12/1993 | Richards et al. | 128/666 |
| 5,279,295 | 1/1994 | Martens et al. | 128/633 |

OTHER PUBLICATIONS

Nonin Brochure on 8604F0 Pulse Oximeter.
Invivo Brochure on 4500 MRI Pulse Oximeter.
Set-Up Excerpt from Nonin Brochure.
Documents re: FDA recall of Nonin Oximeters.

*Primary Examiner*—Lee S. Cohen
*Assistant Examiner*—Robert L. Nasser, Jr.
*Attorney, Agent, or Firm*—Amster, Rothstein & Ebenstein

[57] ABSTRACT

An optical sensor system (such as an oximeter system) for use on a patient in an electrical environment (such as an RF field) includes at least one of the following three subsystems: (A) A light input subsystem includes a first control and display module disposed remotely outside of an electrical field, and input electrical cable connected at one end to the first module and at the other end to an electrically-powered light source disposed closely adjacent but outside of the electrical field. Input fiber optic cable for the transmission of analog optical signals extends from the light source to adjacent a patient in the electrical field. (B) A light output subsystem includes output fiber optic cable for the transmission of analog optical signals extending from adjacent the patient in the electrical field to a light detector disposed closely adjacent but outside of the electrical field. Output electrical cable is connected at one end to the light detector and at the other end to a second control and display module disposed remotely outside the electrical field, (C) A combination of the light input and output subsystems.

7 Claims, 1 Drawing Sheet

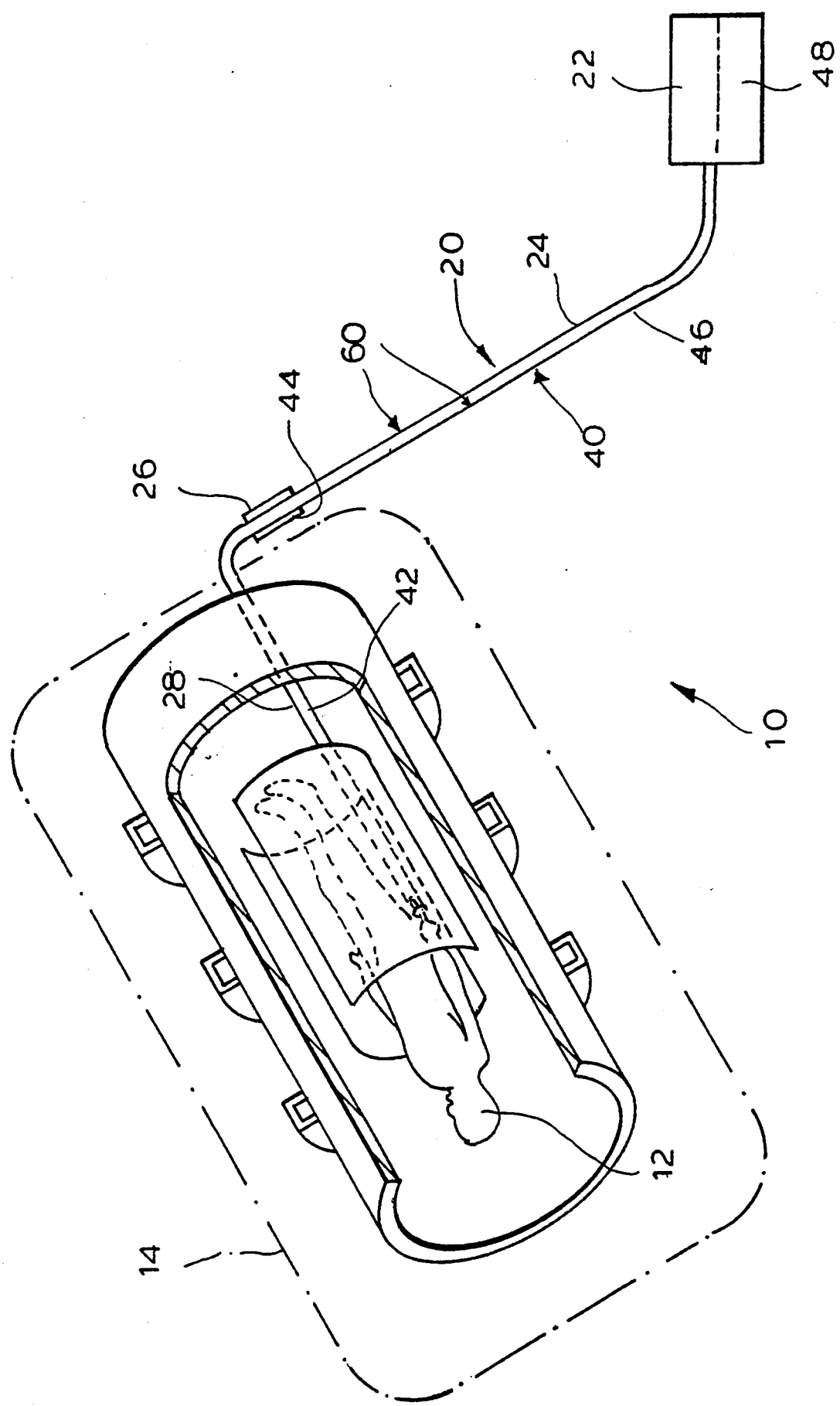

OPTICAL SENSOR SYSTEM

BACKGROUND OF THE INVENTION

The present invention relates to an optical sensor system such as oximeter, and more particularly to such a system designed for use in a radio frequency (RF) environment or other environment requiring electrical isolation of the patient.

Many applications exist where it is desirable to deliver and/or receive light in diagnosing or treating patients. In many cases the light source and light detecting apparatus can be located close to the patient. For example, in the case of patient monitoring with conventional pulse oximetry, light emitting diodes (LEDs) and a photodetector are located on opposite sides of and proximate to a patient's finger. The LEDs and the photodetector are controlled by electrical wires which extend to a control and display module. The absorption of light by tissue and blood in the finger is detected and analyzed to measure the patient's heart rate and oxygen saturation.

Using conventional pulse oximetry in the operating room or during magnetic resonance imaging (MRI) examination can be difficult to implement, dangerous for the patient and/or ineffective due to environmental interaction with wires attached to the LEDs and photodetector. In these cases and others involving electric fields, such as RF fields, it can be advantageous to couple the light using fiber optic light guides (e.g., optical fiber bundles) to preclude electrical interaction with the RF or other electrical field.

In the prior art, two pulse oximeter systems have been developed using fiber optic sensors. Both of these designs have limitations, and neither effectively solves the problem of providing adequate patient isolation with good instrument performance.

Nonin Medical developed the 8604FO Pulse Oximeter with fiber optic sensors composed of two fibers. One fiber was used to deliver light to the patient; another was used to receive light from the patient. Invivo Research developed the 4500 MRI Pulse Oximeter with sensors using one optical fiber and one electrical wire bundle. The fiber provided isolation from the light source, but not the photodetector. In both of these systems, the optical fiber sensors were connected between the control and display module and the patient. Because the oximeter contained some ferrous material and because it was desirable to locate the module close to the viewing window, optical fibers were 30 feet long for Nonin and 17 feet long for Invivo.

Both oximeter system designs fail to combine adequate performance with the desired patient isolation. The Invivo Oximeter provides oxygen saturation measurements with a specified accuracy for saturation between 70 and 100%. While the performance is good, the sensor still contains wires which can create a safety concern for the patient. The Nonin oximeter provides the desired patient isolation, but was recalled by the FDA in July, 1992 for ". . . inaccurate arterial blood oxygen saturation readings . . . ."

While the typical MRI environment presents dangers both from the magnetic field and the radio frequency (RF) field associated with the equipment when it is turned on, it is primarily the RF field which is of concern since this can result in burning of the patient and inaccuracies in the reading due to interaction with the electrical fields associated with the oximeter. The magnetic field presents a problem mainly in that objects of a metallic nature may unexpectedly respond to the field and move with considerable speed under the field influence.

Accordingly, it is an object of the present invention to provide an optical sensor system for use on a patient in an MRI or other electrically isolated environment.

Another object is to provide such a system which combines adequate patient isolation with good instrument performance.

A further object is to provide such a system which is easy and economical to manufacture, maintain and use.

SUMMARY OF THE INVENTION

It has now been found that the above and related objects of the present invention are obtained in an optical sensor system for use on a patient in an electrically isolated environment, the system including at least one of the following: a light input subsystem, a light output subsystem, and a combination of the light input and output subsystems.

The light input subsystem comprises a first control and display module disposed remotely outside of an electrical field, and input electrical cable connected at one end to the module and at the other end to an electrically-powered light source. An electrically-powered light source is disposed closely adjacent but outside of the electrical field and connected to the input electrical cable other end, and input fiber optical cable for the transmission of analog optical signals extends from the light source to adjacent a patient in the electrical field.

The light output subsystem comprises an output fiber optical cable for the transmission of analog optical signals extending from adjacent the patient in the electrical field to a light detector, and a light detector disposed closely adjacent but outside of the electrical field and connected to the output fiber optic cable. Output electrical cable is connected at one end to the light detector and at the other end to a second control and display module, and a second control and display module is disposed remotely outside the electrical field and connected to the output electric cable other end.

In a preferred embodiment, the input fiber optic cable is shorter than the input electrical cable and less than 8 feet. The output fiber optic cable is shorter than the output electrical cable and less than 8 feet. The light source, the light detector, and the modules are typically elements of an oximeter system. The electrical field is typically an RF field. In the combination, the first module is typically the second module.

BRIEF DESCRIPTION OF THE DRAWING

The above and related objects, features, and advantages of the present invention will be more fully understood by reference to the following detailed description of the presently preferred, albeit illustrative, embodiments of the present invention when taken in conjunction with the accompanying drawing wherein the figure is a schematic view of an optical sensor system according to the present invention in use on a patient in an electrical environment.

DETAILED DESCRIPTION OF THE PREFERRED EMBODIMENTS

As the optical signals transmitted to and/or from an oximeter or like device are necessarily analog in nature (rather than digital), the analog optical signals undergo an unacceptable degree of attenuation during their transmission through the light guides (e.g. optical fibers) over extensive distances and emerge with such decreased light intensity that inaccurate readings may result. (By way of contrast, digital optical signals (i.e., on or off signals) are easily accurately read even after severe attenuation.) Accordingly, the present invention minimizes the distance over which the analog optical signals must be transmitted by light guides while maintaining the patient-module separation.

Referring now to the drawing, therein illustrated is an optical sensor system according to the present invention, generally designated by the reference numeral 10. The system 10 is illustrated in use on a patient 12 disposed in an electrical field 14 such as the RF field associated with a magnetic resonance imaging (MRI) system. The optical sensor system 10 includes at least one of the following three subsystems: a light input subsystem generally designated 20, a light output system generally designated 40, or a combination of the light input and light output systems generally designated 60.

The light input subsystem 10 comprises a first control and display module 22 disposed remotely outside of the electrical field 14. The control and display module 22 is conventional in nature for the particular application, and hence need not be described in further detail. The module 22 is disposed sufficiently remotely of the electrical field 14 about the patient so that it neither influences nor is influenced by that electrical field to any appreciable degree. An input electrical cable 24 is connected at one end to the module 22 and at the other end to an electrically-powered light source 26. The light source 26 is disposed closely adjacent but outside of the electrical field 14 about the patient and, as noted, is connected to the input electrical cable 24 at the other end thereof. Thus the input electrical cable 24 provides electrical signals from the module 22 to the light source 26, which acts as a transducer to convert the electrical signals from the module 22 into analog light signals. An input fiber optic cable 28 for the transmission of analog optical signals extends from the light source 26 to adjacent the patient 12 in the electrical field 14. The input fiber optic cable 28 is shorter than the input electrical cable 24 and is preferably less than 8 feet. Because the analog electrical signal travels a relatively short distance within the input fiber optic cable 28, attenuation of the analog electrical signal is less than would be the case if the light source 26 were part of the control and display module 22 and the input fiber optic cable 28 had to extend from the patient 12 in the electrical field 14 all the way to the module 22 disposed remotely outside of the electrical field 14.

Referring still to FIG. 1, the light output subsystem 40 comprises an output fiber optic cable 42 for the transmission of analog optical signals extending from adjacent the patient 12 in the electrical field 14 to a light detector 44. The light detector 44 is disposed closely adjacent but outside of the electrical field 14 about the patient 12 and is connected to the output fiber optic cable 42. The light detector 44 converts the analog light signals received from the output fiber optic cable 42 and, acting as a transducer or photosensor, converts them to analog electrical signals impressed on the output electrical cable 46. An output electrical cable 46 is connected at one end to the light detector 44 and at the other end to a second control and display module 48. The second control and display module 48 is disposed remotely outside the electrical field and connected to the output electrical cable 46 at the other end thereof. The output fiber optic cable 42 is shorter than the output electrical cable 46 and preferably less than 8 feet. Because of the relatively short length of the output fiber optic cable 42, the analog light signals are attenuated therein much less than would be the case if the light detector 44 were disposed in the second control and display module 48 and the output fiber optic cable 42 had to extend all the way from the patient 12 in the electrical field 14 all the way to the second control and display module 48.

The combination 60 comprises in combination the light input subsystem 20 and the light output subsystem 40 in combination. Typically, although not necessarily, in the combination 60 the first module 22 is also the second module 48.

In the preferred embodiment of the present invention illustrated, the optical sensor system 10 is an oximeter system and the electrical field 14 in which the patient 12 is disposed is the RF field accompanying the magnetic field of a magnetic resonance imaging system. The modules 22, 48 are the control and display modules associated with the oximeter system 10. The analog optical signals outputted by the input fiber optic cable 28 is directed through a patient's finger, toe or the like. The analog optical signals inputted into the output fiber optic cable 42 are the analog optical signals outputted from input fiber optic cable 28 after they have passed through the finger or toe of the patient with at least partial absorption of the light by tissue and blood in the finger or toe. The analog optical signals received from the patient's finger or toe, after conversion to electrical signals, are then analyzed by the second module 48 to determine the patient's heart rate and oxygen saturation.

It will be appreciated by those skilled in the art that the optical sensor system of the present invention may be utilized in connection with other diagnosis or treatment apparatus than an oximeter, and that the electrical environment about the patient from which the optical sensor must be isolated may be an electrical field other than an RF field.

The optical sensor system of the present invention includes a totally fiber optic sensor configured to be used in conjunction with an electrical extension cable on at least one end thereof, and preferably both ends. The optical sensor is provided with fiber optic cables which are only long enough to extend from the patient to outside the electrical field and thus only long enough to provide the required isolation for the patient (typically less than 8 feet). The electrical cables connect the fiber optic cables of the optical sensor with the control and display module(s), thereby allowing the latter to be remotely disposed from the electrical field about the patient. Accordingly, the present invention minimizes attenuation of analog optical systems in the fiber optic cables of the optical sensor and utilizes electrical cables to provide communication between the remotely disposed modules and the fiber optic cables of the optical sensor. The electrical signals undergo little, if any, attenuation within the electrical cables over the short distances involved (typically less than 100 feet).

Those familiar with the Nonin 8604FO Pulse Oximeter will appreciate that the present invention utilizes the fiber optic medium only as required to provide isolation from the electrical field about the patient and thereby minimizes attenuation of the analog optical signals within the fiber optic medium while elsewhere utilizing an electrical medium which does not present the same attenuation problems. Thus, whereas the Nonin transmission is over 30 feet each way in the fiber optic medium, the present invention typically utilizes a maximum of 8 feet of optical fiber medium transmission in each direction, thereby greatly reducing the attenuation problem.

As each of the individual elements of the present invention—that is, electrical cables, fiber optic cables, light detectors (photosensors which convert analog light signals into electrical signals), light emitters (which convert electrical signals into analog light signals), and control and display modules—are individually well known in the art, it is deemed unnecessary to specify herein further details thereof.

It is appreciated that electrical fields (such as RF fields) have no sharp termination or boundary lines. Accordingly, it will be understood that reference to an element being disposed "closely adjacent and outside the electrical field" or "remotely outside the electrical field" must be interpreted as meaning that the element is disposed where the electrical field is so attenuated that, as a practical matter, the electrical field does not interfere with operation of the element and operation of the element does not interfere with the function of the electrical field.

To summarize, the present provides an optical sensor system for use on a patient in an RF or other electrical environment and combines adequate patient isolation with good instrument performance. The system is easy and economical to manufacture, maintain and use.

Now that the preferred embodiments of the present invention have been shown and described in detail, various modifications and improvements thereon will become readily apparent to those skilled in the art. Accordingly, the spirit and scope of the present invention is to be construed broadly and limited only by the appended claims, and not by the foregoing specification.

I claim:

1. An optical sensor system for use on a patient in an electrical field, said system including one of the following subsystems:
   (A) a light input subsystem comprising:
      (i) a first control module;
      (ii) an electrically powered light source;
      (iii) an input electrical cable connecting said first control module to said light source;
      (iv) an input fiber optic cable having a first end connected to said light source for the transmission of analog optical signals and having a second end adapted to be disposed at a point adjacent the patient;
      said input fiber optic cable having a sufficient length such that, when said input fiber optic cable second end is disposed at the point adjacent the patient, said light source is disposed closely adjacent, but outside of the electrical field;
      said input electrical cable having a sufficient length such that, when said light source is disposed closely adjacent, but outside of the electrical field, said first control module is disposed remotely outside of the electrical field; and
      said length of said input electrical cable being longer than said length of said input fiber optic cable;
   (B) a light output subsystem comprising:
      (i) a second control module;
      (ii) a light detector;
      (iii) an output electrical cable connecting said second control module to said light detector;
      (iv) an output fiber optic cable having a first end adapted to be disposed at a point adjacent the patient and a second end connected to said light detector for the transmission of analog optical signals;
      said output fiber optic cable having a sufficient length such that, when said output fiber optic cable first end is disposed at the point adjacent the patient, said light detector is disposed closely adjacent, but outside of the electrical field;
      said output electrical cable having a sufficient length such that, when said light detector is disposed closely adjacent, but outside of the electrical field, said second control module is disposed remotely outside of the electrical field; and
      said length of said output electrical cable being longer than said length of said output fiber optic cable;
   (C) a combination of said light input and output subsystems.

2. The system of claim 1, wherein the length of said input fiber optic cable is less than 8 feet.

3. The system of claim 1, wherein the length of said output fiber optic cable is less than 8 feet.

4. The system of claim 1, wherein in combination (C), said light source, said first control module, said light detector, and said second control module are operatively associated with each other as part of a pulse oximeter.

5. The system of claim 1, wherein the first and second control modules are integral with each other.

6. An oximeter system for use on a patient in an MRI environment including an RF field, said system including one of the following subsystems:
   (A) a light input subsystem comprising:
      (i) a first control module;
      (ii) an electrically powered light source;
      (iii) an input electrical cable connecting said first control module to said light source;
      (iv) an input fiber optic cable having a first end connected to said light source for the transmission of analog optical signals and having a second end adapted to be disposed at a point adjacent the patient;
      said input fiber optic cable having a sufficient length such that, when said input fiber optic cable second end is disposed at the point adjacent the patient, said light source is disposed closely adjacent, but outside of the RF field;
      said input electrical cable having a sufficient length such that, when said light source is disposed closely adjacent, but outside of the RF field, said first control module is disposed remotely outside of the RF field; and
      said length of said input electrical cable being longer than said length of said input fiber optic cable;
   (B) a light output subsystem comprising:
      (i) a second control module;
      (ii) a light detector;

(iii) an output electrical cable connecting said second control module to said light detector;
(iv) an output fiber optic cable having a first end adapted to be disposed at a point adjacent the patient and a second end connected to said light detector for the transmission of analog optical signals;
said output fiber optic cable having a sufficient length such that, when said output fiber optic cable first end is disposed at the point adjacent the patient, said light detector is disposed closely adjacent, but outside of the RF field;
said output electrical cable having a sufficient length such that, when said light detector is disposed closely adjacent, but outside of the RF field, said second control module is disposed remotely outside of the RF field; and
said length of said output electrical cable being longer than said length of said output fiber optic cable; and (C) a combination of said light input and output subsystems wherein said first and second control modules are integral with each other.

7. The system of claim 6, where the length of said input fiber optic cable is less than 8 feet and the length of said output fiber optic cable is less than 8 feet.

* * * * *